United States Patent [19]

Mayer et al.

[11] Plant 4,336

[45] Nov. 28, 1978

[54] KENTUCKY BLUEGRASS

[75] Inventors: Eugene W. Mayer, Marysville, Ohio; Torao T. Fuchigami, Long Beach, Calif.

[73] Assignee: The O. M. Scott & Sons Company, Marysville, Ohio

[21] Appl. No.: 864,876

[22] Filed: Dec. 27, 1977

[51] Int. Cl.[2] ..... A01H 5/12

[52] U.S. Cl. ..... Plt./88

[58] Field of Search ..... Plt./88

*Primary Examiner*—Robert E. Bagwill

*Attorney, Agent, or Firm*—J. B. Raden; H. J. Holt

[57] ABSTRACT

A variety of Kentucky bluegrass having a good level of disease resistance and in particular to the leaf spot diseases. The variety provides a desirable dark blue green color throughout the growing season, a color which is accented during cool periods of the year as found in spring and fall months. The variety produces a thick dense turf and persists throughout the growing season under a wide range of environmental conditions.

4 Drawing Figures

SUMMARY OF THE VARIETY

The present invention relates to a new and distinct variety of *Poa pratensis* which has been designated Ba 62-55-M and is now named Merit Kentucky bluegrass. Merit plant material was one of several biotypes selected out of an old established turf area in southern California. Turf performance evaluations of these types were made which resulted in selecting the best turf type. This final selection resulted in one plant type which is now called Merit. Seed of Merit was produced first at Marysville, Ohio, then Salem and Gervais, Oreg. This seed was used to plant turf trials for evaluation of turf performance. Variety evaluation trials were established at Marysville, Ohio; Accokeek, Md.; Long Beach and Somis, Calif.; Gervais, Oreg.; St. Louis, Mo.; Bolton, Mass. and the province of Ontario, Canada.

Merit Kentucky bluegrass reproduces asexually both by propagules (tillers and rhizomes) and disseminules (modified coryopses produced by agomospermy) and has consistently produced progeny plants indistinguishable from the mother plant.

Merit has a number of highly desirable characteristics including a good level of resistance to Helminthosporium spp and *Sclerotinia homoeocarpa*, has a decumbent growth habit and will tolerate low heights of cut. It has a pleasing dark blue green color and produces a good dense turf that persists over a wide range of environmental conditions.

DETAILED DESCRIPTION OF THE VARIETY

Figure 1:
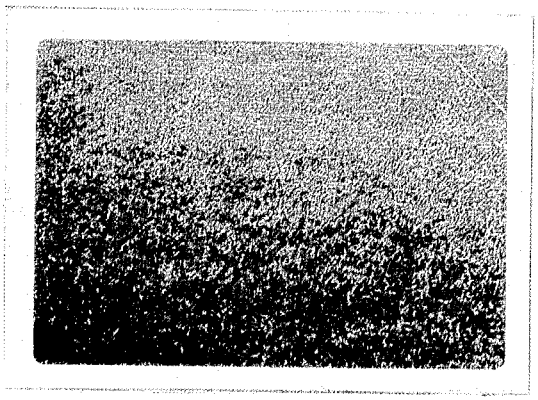
FIG. 1 is a photograph of Merit Kentucky bluegrass maintained under turf management conditions.
Figure 2:
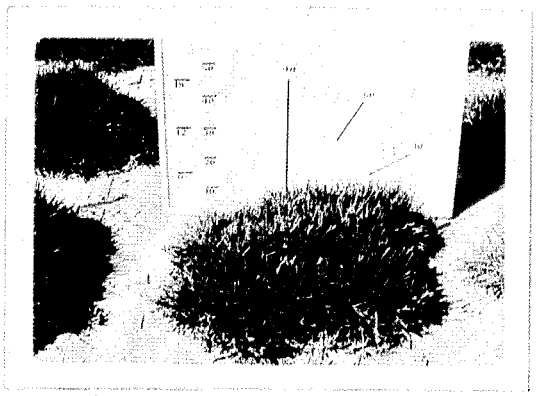
FIG. 2 is a Merit Kentucky bluegrass clone in early spring at Gervais, Oreg.
Figure 3:
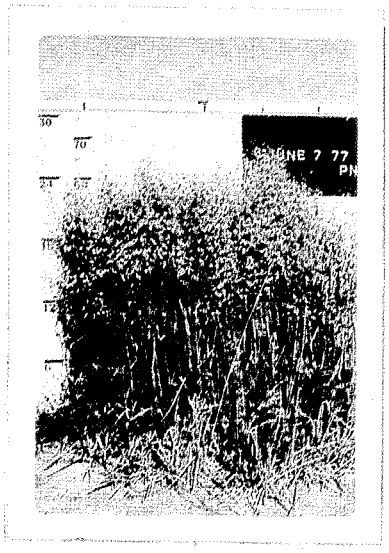
FIG. 3 is a Merit Kentucky bluegrass clone after anthesis at Gervais, Oregon.
Figure 4:
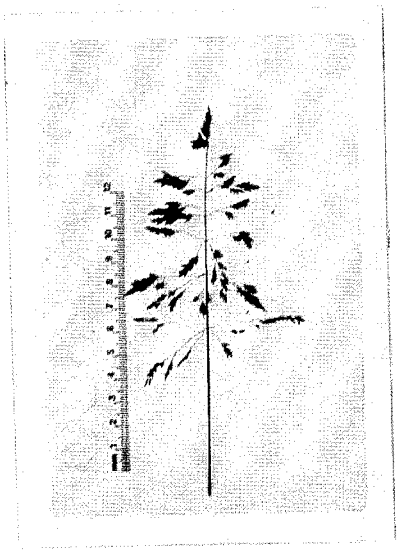
FIG. 4 is a Merit Kentucky bluegrass panicle.

The morphological characteristics of Merit and other commercially available bluegrass varieties are compared in Table 1. As shown by Table 1, the morphological characteristics of Merit afford a basis for distinguishing it from other bluegrass varieties.

TABLE 1

MORPHOLOGICAL COMPARISON OF MERIT AND OTHER KENTUCKY BLUEGRASS VARIETIES

| Variety | Panicle Length in cm. | No. of Panicle Branch Whorls | No. of Branches Per Whorl | | No. of Spikelets Per Whorl | | No. of Nodes Per Plant Stem |
|---|---|---|---|---|---|---|---|
| | | | Lowest | 3rd | Lowest | 3rd | |
| Merit | 9.0 | 8.4 | 5.4 | 4.2 | 52.6 | 29.6 | 1.8 |
| Merion | 10.3 | 7.2 | 3.4 | 3.4 | 42.2 | 27.6 | 2.6 |
| Newport | 10.9 | 9.4 | 3.8 | 3.6 | 33.6 | 18.8 | 2.4 |
| Bristol | 11.7 | 8.4 | 3.4 | 2.6 | 38.0 | 23.2 | 4.0 |

| Variety | Length of Top Internode in cm. | No. of Florets Per Spikelet | Leaf Blade Width* Measured 2 cm. From end of Boat Tip Leaf |
|---|---|---|---|
| Merit | 22.2 | 4.98 | 2.50 mn |
| Merion | 33.6 | 3.98 | 2.07 mn |
| Newport | 38.6 | 3.02 | 2.39 mn |
| Bristol | 34.9 | 5.42 | 2.52 mn |

*Leaf blade width of plants maintained under mowed turf conditions (3.8 cm to 6.4 cm)

Mowed plots have been evaluated under turf conditions in many different tests and at numerous locations. Turfgrass performance information presented indicates the distinctiveness of Merit compared to other bluegrass varieties and its desirable characteristics and persistence.

Seed germination rate and seedling establishment are important factors in a new seedling. Kentucky bluegrasses are recognized for their slowness to germinate and establish compared to other turfgrass species. Differences do occur in germination rates between Kentucky bluegrass varieties. The variety Merion has been rated as slow to germinate whereas the variety Park is normally considered as a faster germinating bluegrass variety. In controlled laboratory tests and field evaluations Merit was rated above Merion and equal to Park in controlled conditions and below Park in actual field conditions. See Tables 2, 3 and 4.

TABLE 2.

AVERAGE GERMINATION PERCENTAGES OF VARIOUS KENTUCKY BLUEGRASS VARIETIES UNDER CONTROLLED CONDITIONS USING LABORATORY GERMINATING CABINET.

| Variety | Days After Seeding | | | |
|---|---|---|---|---|
| | 7 | 10 | 15 | 21 |
| Merit | 55% | 77% | 81% | 85% |
| Victa | 54% | 71% | 83% | 88% |

TABLE 2.-continued

AVERAGE GERMINATION PERCENTAGES OF VARIOUS KENTUCKY BLUEGRASS VARIETIES UNDER CONTROLLED CONDITIONS USING LABORATORY GERMINATING CABINET.

| Variety | Days After Seeding | | | |
|---|---|---|---|---|
| | 7 | 10 | 15 | 21 |
| Park | 50% | 65% | 81% | 85% |
| Merion | 14% | 24% | 60% | 72% |

Rating Scale: Number indicates percent of seeds that germinated.
Germinating Conditions:
Temperature 15° C. for 16 hours - dark
25° C. for 8 hours - light
100 seeds per replication - 3 replications

TABLE 3.

AVERGE GERMINATION PERCENTAGES OF VARIOUS KENTUCKY BLUEGRASS VARIETIES SEEDED IN MID SUMMER UNDER FIELD CONDITIONS.

| Variety | Days After Seeding | | |
|---|---|---|---|
| | 6 | 8 | 15 |
| Merit | 0% | 25% | 78% |
| Victa | 0% | 42% | 78% |
| Park | 0% | 43% | 84% |
| Merion | 0% | 19% | 65% |

Rating Scale:
Number indicates percent germination made by visual estimates of three replications.

TABLE 4.

AVERAGE GERMINATION PERCENTAGES OF VARIOUS KENTUCKY BLUEGRASS VARIETIES SEEDED IN LATE FALL UNDER FIELD CONDITIONS.

| Variety | Days After Seeding | | |
|---|---|---|---|
| | 8 | 21 | 32 |
| Merit | 0% | 59% | 78% |
| Victa | 0% | 80% | 90% |
| Park | 0% | 70% | 83% |
| Merion | 0% | 37% | 64% |

Rating Scale:
Number indicates percent germination by visual estimates of three replications.

Leafspot (Helminthosporium spp) diseases causes severe plant damage and thinning of bluegrass turf in most locations in the Northern United States and Canada during the months of April, May and June of each year. Table 5 provides leaf spot information in the spring on two year old turf grown at Marysville, Ohio. Merion and Fylking are recognized as having an acceptable and a good level of resistance to leaf spot diseases. The common types of Kentucky bluegrass varieties such as Kenblue are quite susceptible to leaf spot disease. In Table 5 Merit is seen to be equal to or slightly lower in resistance than Merion or Fylking but significantly more resistant than Kenblue.

TABLE 5.

LEAF SPOT (Helminthosporium spp) INCIDENCE OF TWO YEAR OLD TURF OF VARIOUS KENTUCKY BLUEGRASS VARIETIES.

| Variety | Percent Leaf Spot | | |
|---|---|---|---|
| | April | May | June |
| Merit | 15% | 23% | 25% |
| Kenblue | 50% | 60% | 50% |
| Merion | 15% | 20% | 15% |
| Fylking | 20% | 20% | 20% |

Rating Scale:
Number indicates percent of leaves infected with leaf spot.

Rating leaf spot diseases for the entire growing season in two consecutive years Merit again demonstrates that it has good resistance compared to other known varieties. See Tables 6 and 7.

TABLE 6.

AVERAGE LEAF SPOT (Helminthosporium spp) INCIDENCE OF ONE YEAR OLD TURF OF VARIOUS KENTUCKY BLUEGRASS VARIETIES.

| Variety | Avg. Percent Leaf Spot Incidence for Entire Year |
|---|---|
| Merit | 22% |
| Kenblue | 48% |
| Merion | 30% |
| Pennstar | 25% |

Rating Scale:
Number indicates percent of leaves infected with leaf spot.

TABLE 7.

AVERAGE LEAF SPOT (Helminthosporium spp) INCIDENCE OF TWO YEAR OLD TURF OF VARIOUS KENTUCKY BLUEGRASS VARIETY.

| Variety | Avg. Percent Leaf Spot Incidence for Entire Year |
|---|---|
| Merit | 31% |
| Kenblue | 63% |
| Merion | 28% |
| Pennstar | 30% |

Rating Scale:
Number indicates percent of leaves infected with leaf spot.

Good leaf spot resistance was also noted in 3 year old turf plots at Accokeek, Maryland. (Table 8).

TABLE 8.

LEAFSPOT (Helminthosporium spp) INCIDENCE OF THREE YEAR OLD TURF OF VARIOUS BLUEGRASS VARIETIES AT ACCOKEEK, MARYLAND.

| Variety | Percent Leaf Spot |
|---|---|
| Merit | 13% |
| Kenblue | 60% |
| Merion | 8% |
| Victa | 10% |

Rating Scale:
Number indicates percent of leaves infected with leaf spot.

Further demonstrating that Merit has a good level of leaf spot resistance over a wide range of environmental conditions seedings were installed in various locations in Ontario, Canada. Table 9 provides leaf spot resistance data of one year old turf in Ontario, Canada, again indicating that the level of resistance is comparable to known resistant varieties.

TABLE 9.

LEAF SPOT (Helminthosporium spp) INCIDENCE IN EARLY SUMMER OF ONE YEAR OLD TURF IN ONTARIO, CANADA, OF VARIOUS KENTUCKY BLUEGRASS VARIETIES

| Variety | Percent Leaf Spot |
|---|---|
| Merit | 10% |
| Kenblue | 44% |
| Merion | 10% |
| Flyking | 4% |

Rating Scale:
Number indicates percent of leaves infected with leaf spot.

Dollar spot (*Sclerotinia homoeocarpa*) is unsightly and can cause damage if infestation is severe. Dollar spot normally occurs in mid to late summer on Kentucky bluegrass and progresses from very small initial spots of dead turf to circular, straw colored areas 2 to 3 inches in diameter. Affected leaves at first show yellow-green blotches, which become water-soaked and finally bleach to a strain colored tan. Merit has shown good resistance to dollar spot with minimum amount of infestation during peak times of the year. Tables 10 and 11 show a good level of dollar spot resistance of Merit compared to other varieties. Fylking and Nugget are normally considered as being susceptible varieties and the common types such as Kenblue being resistant.

TABLE 10.

DOLLARSPOT (*Sclerotinia homoeocarpa*) INCIDENCE OF TWO YEAR OLD TURF OF VARIOUS KENTUCKY BLUEGRASS VARITIES

| Variety | Percent Dollar Spot |
|---|---|
| Merit | 4% |
| Kenblue | 0% |
| Nugget | 20% |

Rating Scale:
Number indicates percent of leaves infected with dollar spot.

TABLE 11.

DOLLAR SPOT (*Sclerotinia homoeocarpa*) INCIDENCE OF VARIOUS KENTUCKY BLUEGRASS VARIETIES AT ACCOKEEK, MARYLAND

| Variety | Percent Dollar Spot |
|---|---|
| Merit | 16% |
| Kenblue | 7% |
| Fylking | 42% |
| Nugget | 23% |
| Merion | 11% |
| Bristol | 5% |

Rating Scale:
Number indicates percent of leaves infected with dollar spot.

Merit can be characterized as moderately slow to green up in early spring (Tables 12 and 13).

TABLE 12.

EARLY SPRING GREEN UP OF VARIOUS KENTUCKY BLUEGRASS VARIETIES

| Variety | Early Spring Color |
|---|---|
| Merit | 4.1 |
| Kenblue | 6.4 |
| Vantage | 6.4 |
| Victa | 4.1 |
| Nugget | 1.8 |

Rating Scale:
1 = straw colored
10 = dark green.

TABLE 13.

EARLY SPRING GREEN UP OF VARIOUS KENTUCKY BLUEGRASS VARIETIES AT ACCOKEEK, MARYLAND

| Variety | Early Spring Color |
|---|---|
| Merit | 3.0 |
| Vantage | 4.0 |
| Kenblue | 4.3 |
| Merion | 2.8 |

Rating Scale:
1 = straw colored
10 = dark green.

Kenblue and Vantage are known to be one of the first to break winter dormancy and turn green with Merion being late and Nugget very late. When greening is complete Merit has a very dark distinctive blue-green color in the spring compared to other varieties. The depth of its color is shown in Table 14.

TABLE 14.

SPRING COLOR OF VARIOUS BLUEGRASS VARIETIES AFTER COMPLETE WINTER DORMANCY HAS BEEN BROKEN AT ACCOKEEK, MARYLAND

| Variety | Spring Color |
|---|---|
| Merit | 9.5 |
| Vantage | 8.0 |
| Kenblue | 7.5 |
| Merion | 9.3 |

Rating Scale:
1 = straw colored
10 = dark green.ps

Merit has a moderate to low vertical growth habit which makes its use as a turfgrass quite acceptable. Clippings are not excessive when maintained at a turf cutting height and mowed at normal frequent intervals such as 7 to 10 days during active growth. This moderate vertical growth habit can be demonstrated from seedling stage to turf use conditions to mature plant height when seed heads are produced (Tables 15, 16 and 17).

TABLE 15.

SEEDLING GROWTH HABIT SIX WEEKS AFTER SEEDING

| Variety | Growth Habit |
|---|---|
| Merit | 1.8 |
| Kenblue | 3.4 |
| Vantage | 2.5 |
| Bristol | 1.8 |

Rating Scale:
1 = low growing
4 = tall.

TABLE 16.

PLANT HEIGHT REGROWTH OF VARIOUS BLUEGRASS VARIETIES ONE WEEK AFTER MOVING AT 38 mm IN AUGUST

| Variety | Plant Height in mm |
|---|---|
| Merit | 86 |
| Kenblue | 96 |
| Merion | 77 |
| Bristol | 69 |
| Newport | 92 |

Rating Scale:
Number indicates length of leaf from ground level to end of leaf.

TABLE 17

MATURE PLANT HEIGHT INCLUDING PANICLE OF VARIOUS KENTUCKY BLUEGRASS VARIETIES GROWN AT MARYSVILLE, OHIO

| Variety | Mature Plant Height in Centimeters |
|---|---|
| Merit | 42 cm. |
| Bristol | 47 cm. |
| Park | 67 cm. |
| Kenblue | 64 cm. |
| Merion | 44 cm. |
| Bonnieblue | 36 cm. |

Rating Scale:
Number indicates length of plant from ground to top of panicle.

Turf quality, a rating taking all turfgrass performance characteristics together and assigning it a value, was measured at Ontario, Canada; Accokeek, Md. and Marysville, Ohio. A rating scale of 1 to 4 was used with 4 being the best turf. Merit is rated as moderate to good performance in all locations, outperforming the common type varieties and slightly below the recognized improved types (Tables 18, 19 and 20).

TABLE 18.

AVERAGE TURF QUALITY RATING FOR ENTIRE GROWING SEASON OF ONE YEAR OLD TURF IN ONTARIO, Canada

| Variety | Avg. Turf Quality Ratings for Entire Growing Season |
|---|---|
| Merit | 2.1 |
| Kenblue | 1.8 |
| Merion | 2.2 |
| Fylking | 2.3 |

Rating:
1 - Poor
4 - Excellent.

TABLE 19.

TURF QUALITY OF TWO YEAR OLD TURF OF VARIOUS KENTUCKY BLUEGRASS VARIETIES IN MAY AT MARYSVILLE, OHIO.

| Variety | Turf Quality |
|---|---|
| Merit | 2.0 |
| Bristol | 2.5 |
| Kenblue | 1.5 |
| Newport | 1.9 |
| Fylking | 2.0 |

Rating Scale:
1 - Poor
4 - Excellent.

TABLE 20.

AVERAGE TURF QUALITY FOR ENTIRE GROWING SEASON OF TWO YEAR OLD TURF AT ACCOKEEK, MARYLAND

| Variety | Turf Quality |
|---|---|
| Merit | 2.6 |
| Merion | 2.8 |
| Victa | 2.9 |
| Kenblue | 2.0 |

Rating scale:
1 - Poor
4 - Excellent.

Ten randomly selected seeds of various varieties were laid end to end to obtain total length of the 10 seeds. Merit was shortest in length (27.5 mm) compared to five other varieties. In measuring these same ten seeds as to width by placing them side by side Merit was second widest (7.5 mm) of the group (Table 21), therefore indicating that Merit seed may be distinguished as being a short wide seed. Merit is further distinguished in that it exhibits high seed-set and high seed yield.

TABLE 21.

SEED LENGTH AND WIDTH OF TEN RANDOMLY SELECTED SEEDS LAYED END TO END AND SIDE BY SIDE RESPECTIVELY OF VARIOUS KENTUCKY BLUEGRASS VARIETIES

| Variety | Length in mm | Width in mm |
|---|---|---|
| Merit | 27.5 mm | 7.5 mm |
| Fylking | 29.8 mm | 7.2 mm |

TABLE 21.-continued

SEED LENGTH AND WIDTH OF TEN RANDOMLY SELECTED SEEDS LAYED END TO END AND SIDE BY SIDE RESPECTIVELY OF VARIOUS KENTUCKY BLUEGRASS VARIETIES

| Variety | Length in mm | Width in mm |
|---|---|---|
| Park | 29.3 mm | 6.5 mm |
| Kenblue | 29.0 mm | 6.7 mm |
| Bristol | 28.7 mm | 8.5 mm |

In seed yield trials under same growing conditions at Gervais, Oreg., differences were noted between varieties in respect to time in heading and anthesis compared to other varieties evaluated (Tables 22 and 23).

TABLE 22.

PERCENT HEADING AT DIFFERENT DATES OF VARIOUS KENTUCKY BLUEGRASS VARIETIES AT GERVAIS, OREGON

| Variety | April 29 | May 3 | May 7 | May 10 | May 17 | May 19 |
|---|---|---|---|---|---|---|
| Merit | | | 2 | 25 | 75 | 95 |
| Vantage | 40 | 90 | 95 | 95 | 100 | 100 |
| Victa | | | 2 | 10 | 45 | 95 |
| Bristol | 5 | 10 | 25 | 90 | 95 | 100 |
| Windsor | | 10 | 50 | 90 | 95 | 100 |

Rating Scale:
Number indicates percent of plants that are heading out.

TABLE 23.

PERCENT ANTHESIS AT DIFFERENT DATES OF VARIOUS KENTUCKY BLUEGRASS VARIETIES AT GERVAIS, OREGON

| Variety | May 21 | May 25 | May 27 | May 30 | June 2 | June 4 |
|---|---|---|---|---|---|---|
| Merit | | 1 | 25 | 25 | 50 | 100 |
| Vantage | 25 | 40 | 60 | 100 | | |
| Victa | | | 1 | 30 | 30 | 100 |
| Bristol | 40 | 80 | 90 | 100 | | |
| Windsor | | | 5 | 30 | 50 | 100 |

Rating Scale:
Number indicates percent of plants that are flowering.

What is claimed and desired to be secured by Letters Patent is:

1. A variety of bluegrass plant, substantially as shown and described, characterized particularly by a high level of resistance to disease and especially leaf spot disease, a desirable dark blue-green color throughout the growing season but particularly during cool periods of the year, a thick dense turf and persistance under a wide variety of environmental conditions.

* * * * *